United States Patent [19]

Kuczynski

[11] Patent Number: 5,722,965
[45] Date of Patent: Mar. 3, 1998

[54] LOW PROFILE OSTOMY SYSTEM WITH REPOSITIONABLE POUCH

[75] Inventor: Thomas J. Kuczynski, Sayreville, N.J.

[73] Assignee: Bristol-Myers Squibb Company, Princeton, N.J.

[21] Appl. No.: 609,318

[22] Filed: Feb. 29, 1996

[51] Int. Cl.$^6$ .................................................. A61F 5/44
[52] U.S. Cl. ........................................ 604/344; 604/338
[58] Field of Search ................................. 604/332, 336, 604/338, 342, 344

[56] References Cited

U.S. PATENT DOCUMENTS

| | | | |
|---|---|---|---|
| 5,496,296 | 3/1996 | Holmberg | 604/344 |
| 5,501,677 | 3/1996 | Jensen | 604/338 |

Primary Examiner—Robert A. Clarke
Attorney, Agent, or Firm—Stuart E. Krieger

[57] ABSTRACT

The low profile ostomy system includes an adhesively securable repositionable pouch that bonds to a body-side mounting wafer. The repositionable pouch is removable from the mounting wafer for repositioning if necessary. In a preferred embodiment of the invention, a resealable tape, which is in the form of a foam tape, is located on a face plate of the pouch and a releasable film, which is backed by a foam tape, is located on a body-side mounting wafer. The face plate of the pouch is formed with an extension tab that is accessible before and after the pouch has been secured to the body-side mounting wafer. The extension tab facilitates peeling of the face plate from the body-side mounting wafer during removal of the pouch from the mounting wafer. The foam tape on the body-side mounting wafer and the face plate inhibit formation of wrinkles or kinks at the engagement surfaces of the face plate and body-side mounting wafer when the pouch is removed from the body-side mounting wafer.

16 Claims, 4 Drawing Sheets

LOW PROFILE OSTOMY SYSTEM WITH REPOSITIONABLE POUCH

BACKGROUND OF THE INVENTION

This invention is directed to low profile ostomy systems, and more particularly to a novel adhesively coupled ostomy system wherein the adhesive engagement surfaces of the coupling members remain substantially wrinkle-free during removal and repositioning of an ostomy pouch around a stoma and pouch separation can be accomplished without stretching the pouch envelope.

When an adhesively securable ostomy pouch of the type shown in European Patent Application Publication 0611122A1 is supported on a mounting wafer that surrounds a stoma, the adhesive connection between a face plate of the pouch and the body-side mounting wafer is generally non-adjustable. In instances where the face plate is not sufficiently concentric with the stoma, it is often desirable to make a further adjustment of the pouch position after it has been adhesively secured to the body-side mounting wafer.

However, removal of an adhesively secured pouch from a body-side mounting wafer can cause the face plate and/or the body-side mounting wafer to wrinkle, especially if the adhesive has a high bond attachment. Wrinkles or kinks in the body-side mounting wafer or in the face plate of the pouch are detrimental to the integrity of the seal between the pouch and wafer. Any wrinkles or kinks can provide a path for undesirable leakage of vapor and material when the face plate of the pouch is resecured to the body-side mounting wafer.

In addition, it is often necessary to manipulate the pouch by the pouch envelope during removal of the pouch from the body-side mounting wafer. Any stresses or strains on the pouch envelope during removal of an adhesively secured pouch for adjustment purposes can weaken or damage the envelope material which may provide a further avenue of leakage.

If adjustment of an adhesively secured pouch envelope is known to be difficult and is known to entail a likely risk of damage or failure of the pouch, there is a strong possibility that pouch adjustment will be discouraged despite discomfort of the user. Such pouches are not likely to be universally acceptable.

It is thus desirable to provide an ostomy system with an adhesively secured pouch that permits easy removal and repositioning of the pouch without damaging the pouch envelope, the pouch face plate or the mounting wafer, and without compromising the leak-tight securement of the pouch during such repositioning. It is also desirable to provide a low profile adhesively installed ostomy system wherein the pouch is relatively easy to manipulate during installation and removal.

OBJECTS AND SUMMARY OF THE INVENTION

Among the several objects of the invention may be noted the provision of a novel low profile ostomy system with an adhesively secured ostomy pouch, a novel low profile ostomy system with an adhesively secured ostomy pouch that is repositionable without compromising a leak-tight seal between the pouch and a body-side mounting wafer, a novel low profile adhesively secured ostomy system wherein the face plate of the pouch can be manipulated relative to the body-side mounting wafer to obtain substantially concentric alignment of the face plate with a body-side mounting wafer, and a novel method of providing wrinkle-free securement, removal and resecurement of an ostomy pouch with a body-side mounting wafer.

Other objects and features of the invention will be in part apparent and in part pointed out hereinafter.

In accordance with the invention, the ostomy system includes a pouch with an adhesively securable face plate that attaches to a body-side mounting wafer. The pouch, which can be closed-end or drainable, is detachable from the body-side mounting wafer for repositioning if necessary.

In order to facilitate repositioning or removal of the pouch after it has been adhesively secured to a body-side mounting wafer, a tab is provided on the face plate of the pouch. The tab is manually accessible after the pouch has been secured to the body-wide mounting wafer. Gripping of the tab facilitates peeling of the face plate from the body-side mounting wafer and also facilitates manipulation, positioning and repositioning of the face plate relative to the body-side mounting wafer. Also, since the peeling force is directed through the face plate of the pouch, there is little, if any, stretching of the pouch envelope during removal and repositioning of the pouch.

The adhesive coupling means for the ostomy system include a resealable tape and a releasable film, one of which is provided on the pouch and the other of which is provided on the body-side mounting wafer.

In a preferred embodiment of the invention, the resealable tape is provided on the pouch and the releasable film is provided on the body-side mounting wafer. The resealable tape on the body-side mounting wafer is in the form of a foam tape, and the releasable film on the body-side mounting wafer is backed by a foam tape as well. The foam tapes on the mounting wafer and the face plate inhibit development of kinks or wrinkles in either the face plate or the mounting wafer during removal and resecurement of the face plate relative to the mounting wafer.

Since the foam tape inhibits formation of wrinkles in the face plate and the mounting wafer, the engagement surfaces on the face plate and the mounting wafer are adhesively secured together in leak-tight fashion, even when the pouch is repositioned several times on the body-side mounting wafer.

The body-side mounting wafer includes an abdominal engagement adhesive for securing the mounting wafer to an abdominal surface. A peripheral edge of the abdominal adhesive is covered by an annular tape that overlays the edge of the abdominal adhesive. The annular overlay tape has an inside diameter that is large enough to expose a landing area of sufficient size on the releasable film to receive the resealable tape of the pouch face plate.

During positioning of the body-Side mounting wafer on the abdominal surface, manipulation portions are provided on opposite sides of the annular overlay tape to facilitate positioning of the mounting wafer on the abdominal surface.

The ostomy system is thus a low profile adhesive securement arrangement that is not bulky, yet is flexible and non-flimsy to ensure that wrinkles and kinks do not develop at the pouch coupling surfaces. Thus, leaks that can result from wrinkles in engageable adhesively secured pouch coupling surfaces do not develop since securement, removal and resecurement of the ostomy pouch to the body-side mounting wafer is a substantially wrinkle-free operation.

The invention also includes a method of providing wrinkle-free securement, removal and resecurement of an adhesive coupling member of an ostomy pouch and a body-side mounting wafer. The method includes providing a landing surface formed of releasable film for the body-side mounting wafer, incorporating within the mounting wafer a layer of foam tape to support the releasable film, providing the face plate of the ostomy pouch with a resealable adhesive coupling for engagement with the releasable film of the body-side mounting wafer, supporting the resealable adhesive with a foam layer and engaging the resealable adhesive of the pouch coupling with the releasable film of the mounting wafer, to permit a detachable coupling of the pouch to the mounting wafer.

The invention accordingly comprises the constructions and method hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

Figure 1:
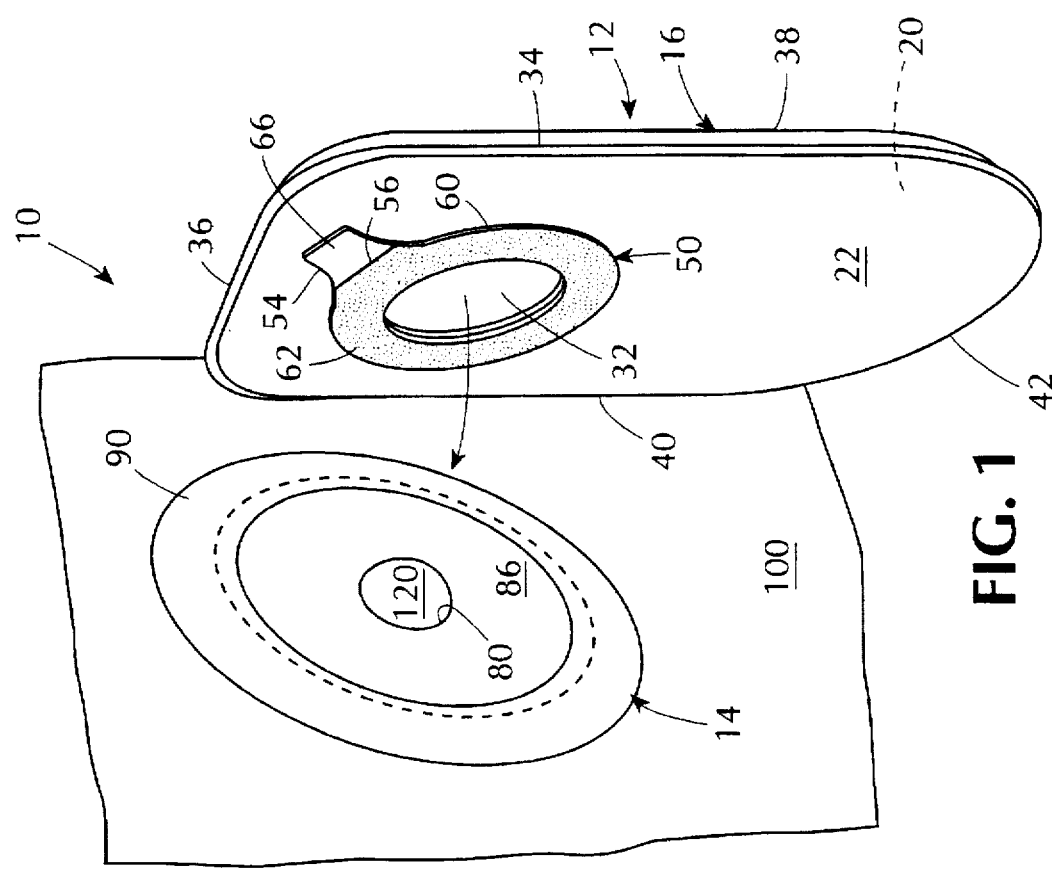
FIG. 1 is a simplified perspective view of an ostomy system incorporating the present invention, prior to adhesive attachment of the ostomy pouch to the body-side mounting wafer.

An ostomy system incorporating one embodiment of the invention is generally indicated by the reference number 10 in FIG. 1.

The ostomy system 10 includes a pouch 12 and a body-side mounting wafer 14 shown in separated position in FIG. 1. The body-side mounting wafer 14 is adhesively secured to an abdominal surface 100 around a stoma 120.

The ostomy pouch 12, which is expandable, is formed of a known envelope 16 of flexible thermoplastic material made in accordance with known techniques in the art of ostomy pouch construction. The pouch material is impermeable to Gas and water.

Figure 2:
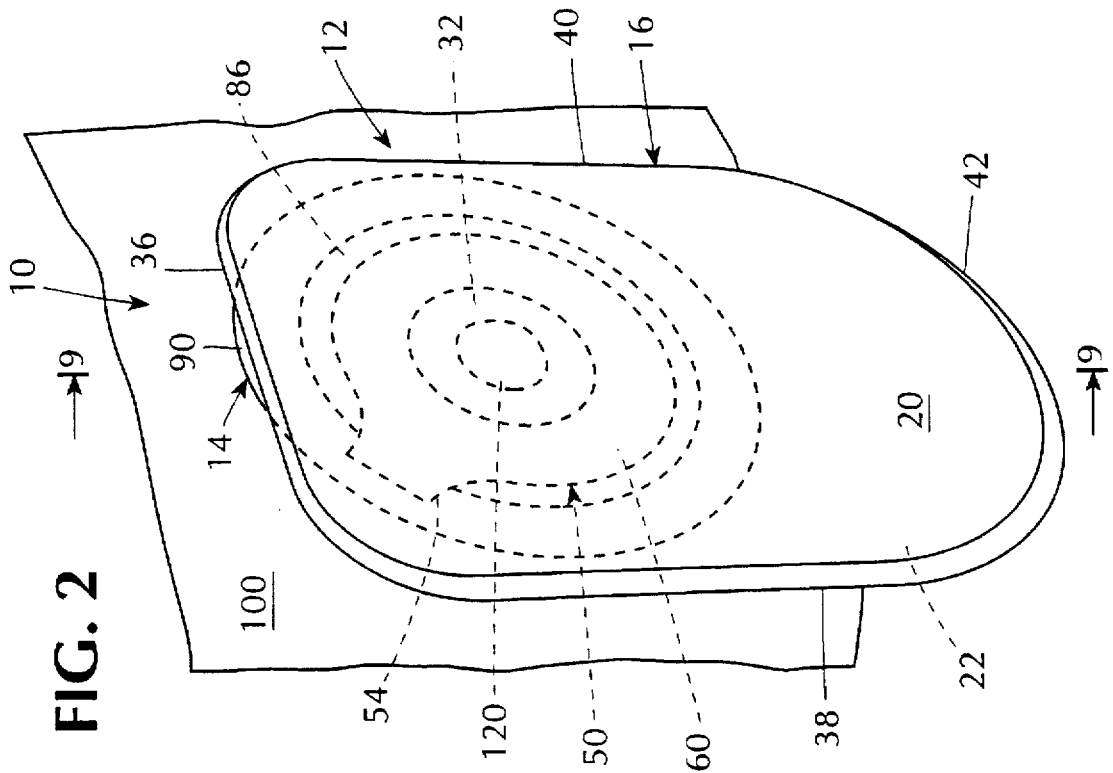
FIG. 2 is a simplified perspective view thereof after the ostomy pouch has been adhesively secured to the body-side mounting wafer.

The pouch envelope 16 includes a front wall 20 (FIG. 2) that faces away from the abdominal surface 100 and a rear wall 22 (FIG. 1) that confronts the abdominal surface 100.

Figure 6:
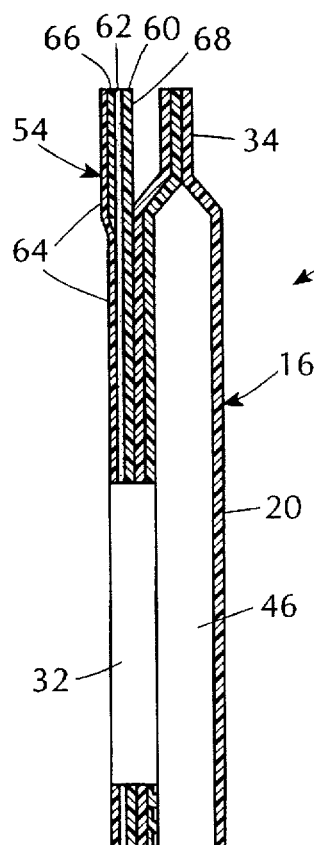
FIG. 6 is a simplified exploded perspective view of the ostomy pouch.
Figure 6:
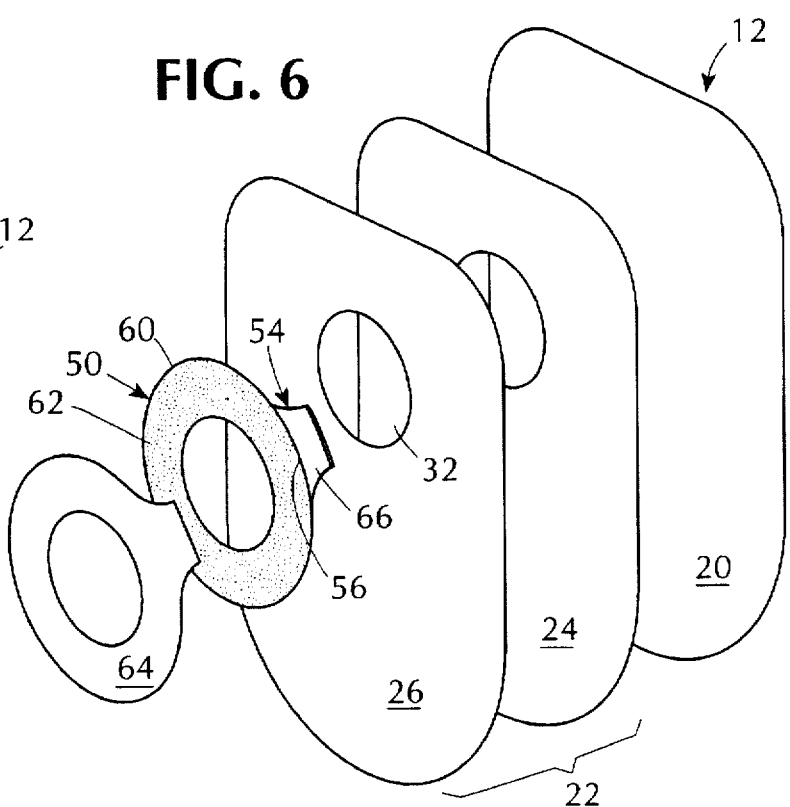

Referring to FIG. 6, the rear wall 22 includes an inside layer 24 of the same material as the front wall 20 and an outside layer 26 of perforated polyethylene flocking to provide a comfortable surface contact between the layer 26 and the abdominal surface 100. As seen in FIG. 6, both the layers 24 and 26 respectively include aligned waste inlet openings 30 and 32. The front and rear walls 20 and 22 of the pouch 12 are joined together by a peripheral thermal weld 34 (FIG. 1). The aligned peripheries of the waste inlet openings 30 and 32 in the layers 24 and 26 are sealed together in any suitable known manner, such as thermal welding.

The pouch envelope 16 further includes a top portion 36 with rounded corners, opposite side portions 38 and 40 that are substantially parallel, and a curved bottom portion 42 that merges into the opposite side portions 38 and 40. The pouch envelope 16 thus defines a waste collection chamber 46 (FIG. 8) accessible through the aligned waste inlet openings 30 and 32 of the rear wall 22.

For purposes of simplicity, the reference number 32 will be used hereinafter to indicate the waste inlet opening of the pouch envelope 16.

Figures 9, 10:
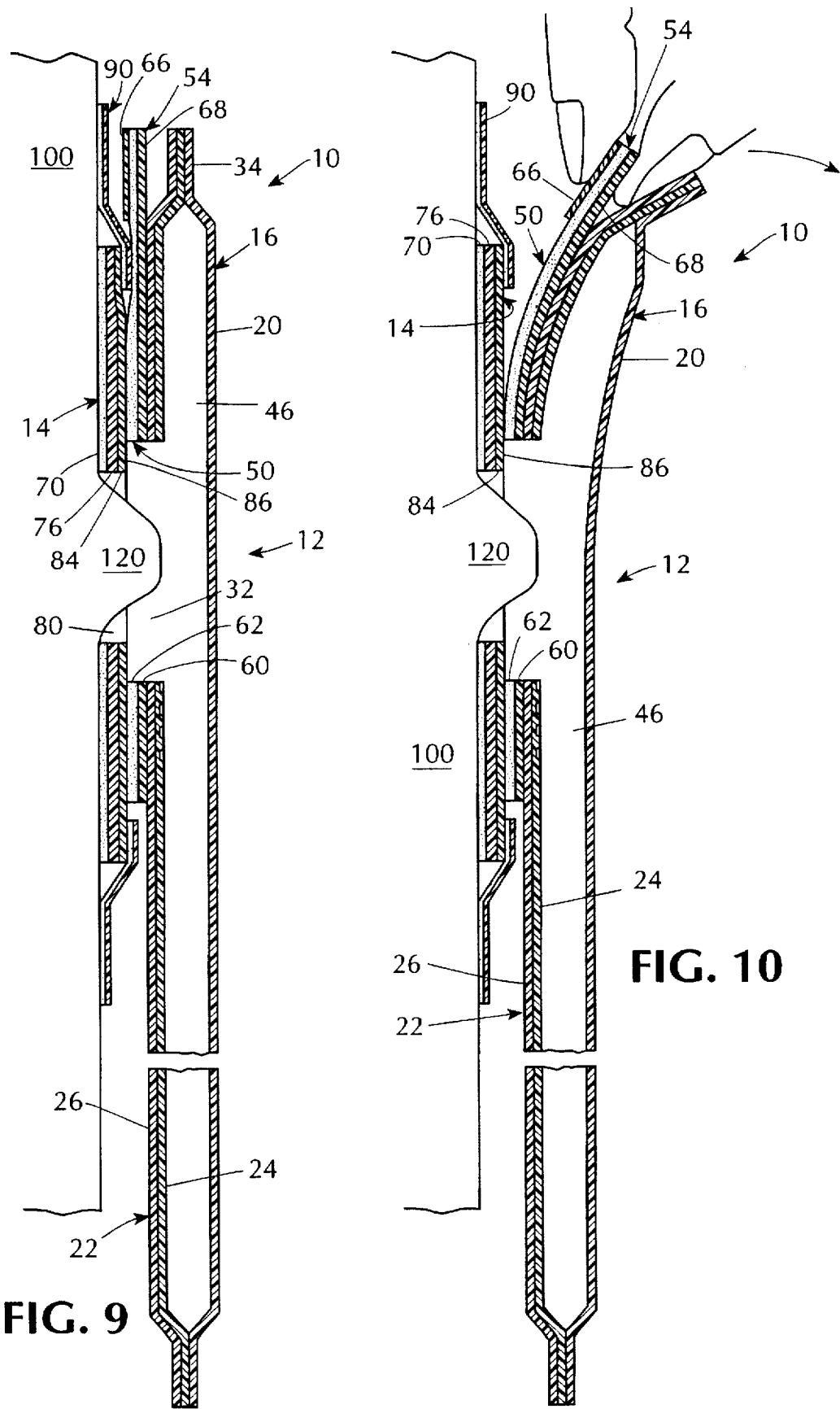
FIG. 9 is a sectional view of the ostomy system on an abdominal wall in alignment with a stoma.
FIG. 10 is a view similar to FIG. 9, showing the ostomy pouch partly detached from the body-side mounting wafer prior to repositioning of the pouch against the wafer.

The waste inlet opening 32 has a diameter of approximately 1¾ inches and is located nearer the top portion 36 of the pouch envelope than the bottom portion The pouch 12 further includes a generally annular adhesive face plate 50 that borders the waste inlet opening 32 and is attached to the rear wall 22 by an annular thermoweld 52 (FIG. 9). The face plate 50 includes a tab projecting beyond a circular periphery 56 of the face plate 50 at an angle of approximately 50° to 60° from the vertical.

The face plate 50 is preferably formed of a resealable foam tape 60, such as the type manufactured by the 3M Company of Minneapolis, Minn. and designated No. 9776 Foam Medical Tape On Liner. The resealable foam tape 60 includes a closed cell polyethylene foam backing approximately 0.08 mm thick with a hypoallergenic pressure-sensitive acrylate adhesive 62 and a silicone release paper 64. The face plate 50 has an inner diameter of approximately 1¾ inches, substantially identical to the inner diameter of the waste inlet opening 32, and an outer diameter of approximately 3⅛ inches.

The tab portion 54 of the face plate 50 includes a film layer 66 (FIG. 8) laminated to the acrylic adhesive 62 of the tab 54. Preferably the film layer 66 is plasticized, flexible polyvinylchloride sheet material 0.010 to 0.080 inches thick, with an outside surface that is non-adhesive to ensure that the tab portion 54 is accessible for manual gripping. The film layer 66 thus reinforces the tab 54 and permits manipulation of the tab 54 without adhesive entanglement.

Figure 8:
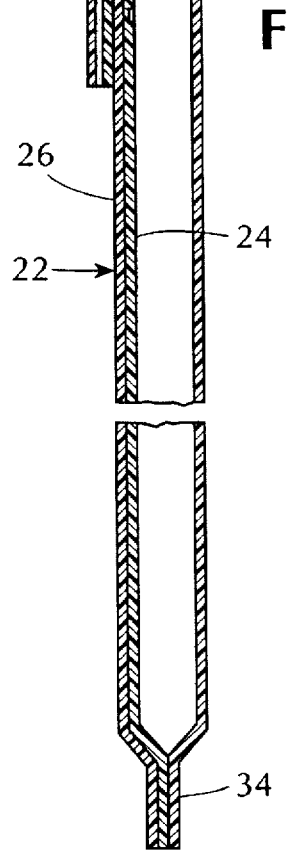
FIG. 8 is a sectional view taken on the line 8—8 of FIG. 7.
Figure 7:
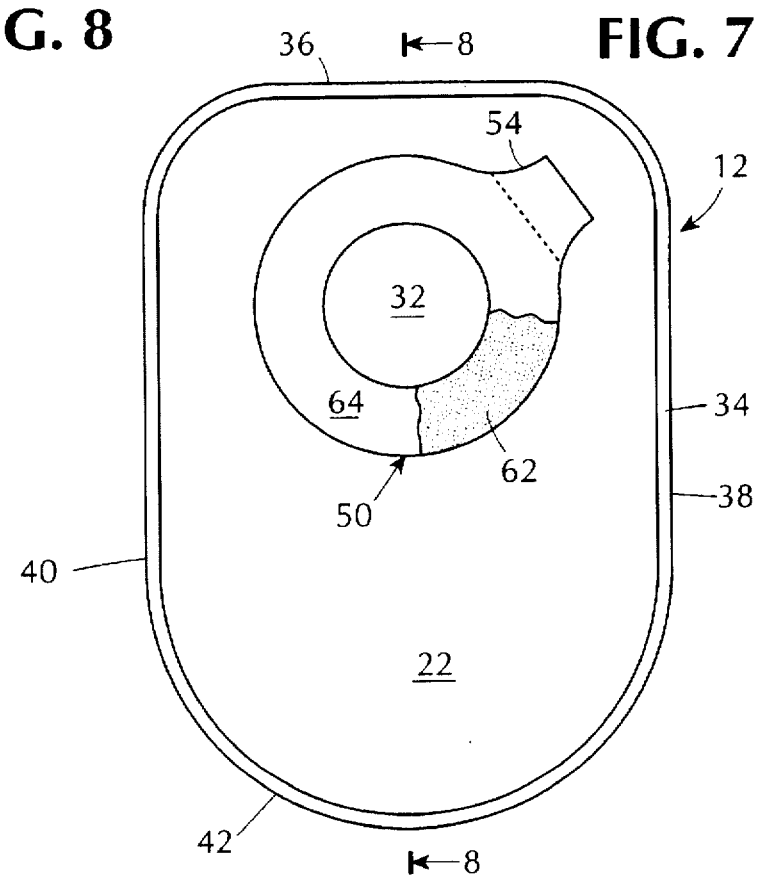
FIG. 7 is a plan view of the components of the ostomy pouch of FIG. 6 in assembled condition.

As most clearly shown in FIGS. 8-10, the surface 68 of the tab portion that confronts the rear wall 22 of the pouch 16 is non-adhesive and is not joined to the rear wall 22 to further ensure that the tab portion 54 is accessible for manual gripping and manipulation.

It has been found that the foam tape 60 for the face plate 50 allows substantially wrinkle-free bending or flexion of the face plate 50. Thus, during peeling of the adhesive attachment of the face plate 50 from the mounting wafer 14 during removal of the pouch 12 from the mounting wafer 14, there are no residual wrinkles or kinks in the adhesive engagement surface 62 of the face plate 50. The film layer 66 on the tab portion 54 reinforces the tab and helps prevent the tab 54 from stretching during peeling of the face plate 50 from the body-side mounting wafer Manipulation or pulling of the tab 54 during removal of the face plate 50 from the mounting wafer 14 permits the peeling force to be directed through the face plate 50, rather than the walls 20 and 22 of the pouch.

As an alternative to using the film layer 66 on the tab 54, the tab 54 can be formed with sufficient elongation to permit doubling over of the tab on itself after the silicone release paper 64 is removed. The doubling over of the tab 54 upon itself will provide reinforcement to the tab and cover the acrylic adhesive 62 on the tab surface.

Alternatively, the face plate 50 can be adhered rather than heat-welded to the pouch wall 22, as by applying pressure-sensitive adhesive to the pouch-confronting side of the face plate 50 to permit an adhesive bond between the face plate 50 and the rear wall 22. Two of the film layers 66 can then be provided on both sides of the tab 54 to cover the adhesive layers on both sides of the tab 54, thereby assuring access of the tab to manual gripping.

The body-side mounting wafer 14 is a generally circular arrangement with a central opening 80 of approximately ¾ inches and an outside diameter of approximately 4 inches. The body-side mounting wafer 14 is thus sized to extend beyond the periphery of the annular face plate 50, as most clearly shown in FIG. 9.

Figure 3:
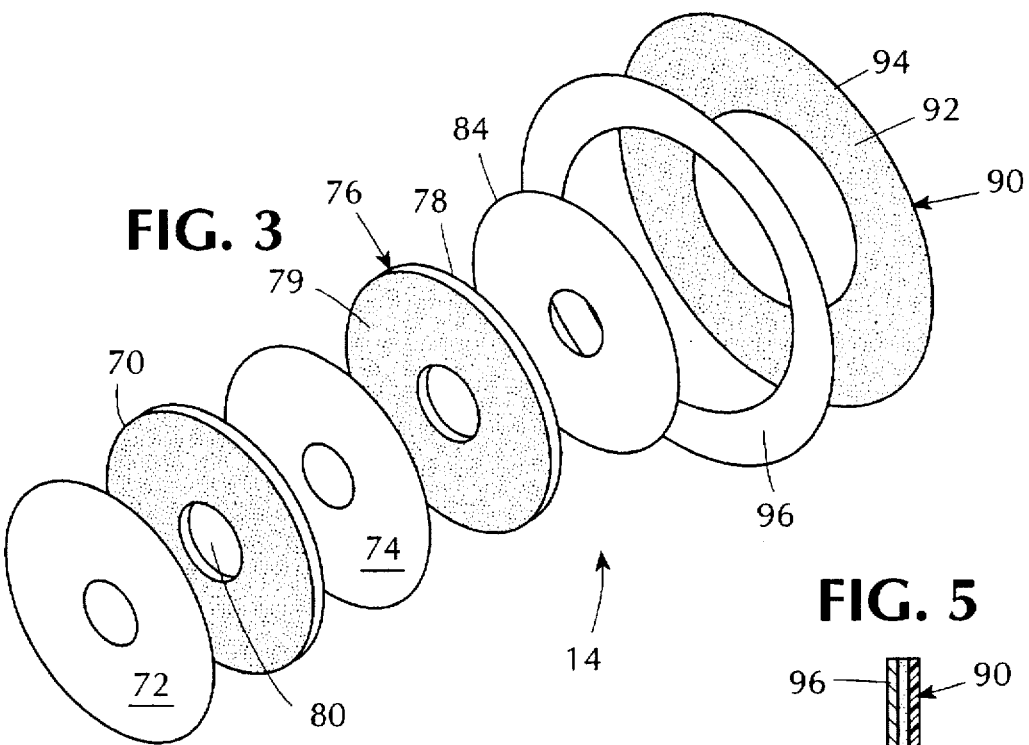
FIG. 3 is an exploded perspective view of the body-side mounting wafer.

Referring to FIG. 3, the body-side mounting wafer 14 includes an annular abdominal adhesive layer 70 covered on both sides with removable layers of silicone release paper 72 and 74 that are removed when the layer 70 is installed on the abdominal surface 100. The layers 72 and 74 are substantially identical in inner and outer diameter to the layer 70. The abdominal adhesive layer 70 is preferably formed of a hydrocolloid adhesive, approximately 0.030 to 0.080 inches thick, such as the type sold under the trademark Stomahesive® or Durahesive® by Bristol-Myers Squibb Company of New York, N.Y.

A composite 76, also substantially identical in inner and outer diameter to the abdominal adhesive layer 70, is in the form of a resealable foam tape of the type manufactured by the 3M Company of Minneapolis, Minn. under the designation 3M Closed Cell Foam 1773. The tape 76 includes a closed cell polyethylene foam backing 78 approximately 0.8 mm thick with a layer 79 of hypoallergenic pressure-sensitive acrylate adhesive that is covered by a layer of silicone release paper similar to the layers 72 and 74. The silicone release paper layers such as 74 are removed prior to assembly of the mounting wafer 14.

A layer 84 of polyethylene release film, which is preferably of the type manufactured by the 3M Company of Minneapolis, Minn. under the designation 3M MSX-1198 Clear PE Release Film, is laminated to the back of the foam tape 76. The opposite surface 86 (FIG. 5) of the release film 84 constitutes a releasable surface-landing area for the resealable adhesive 62 of the annular face plate 50.

Figure 4:
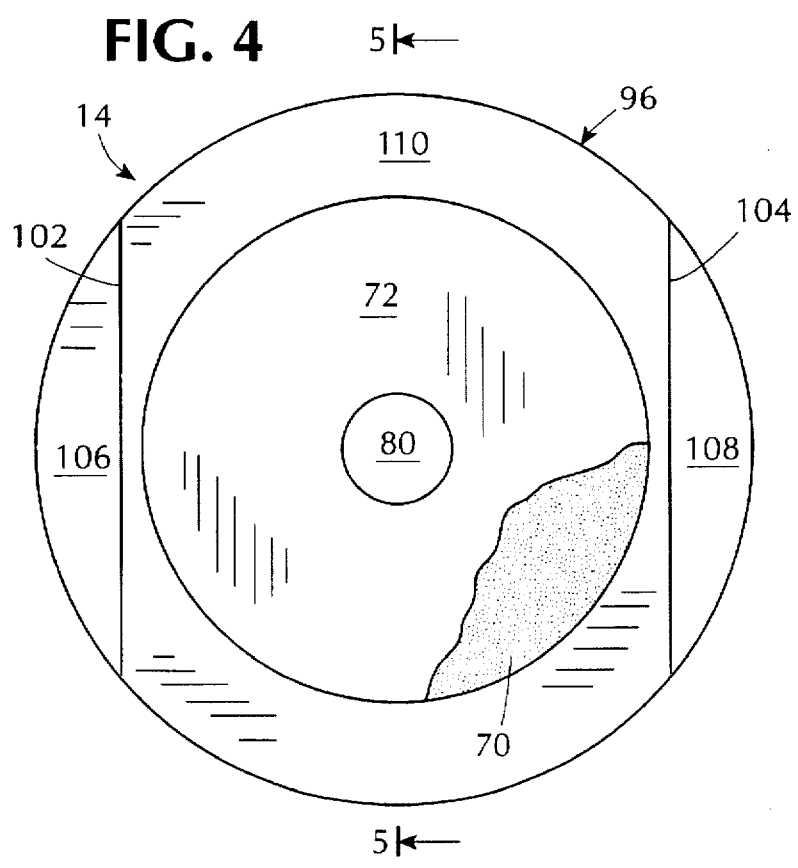
FIG. 4 is a plan view of the body-side mounting wafer in assembled condition.

The body-side mounting wafer 14 further includes a collar 90 formed of Fasson material having an adhesive coating 92 and a soft, perforated non-adhesive backing 94. A silicone release collar 96 (FIG. 3) for the adhesive coating 92 has preformed cut lines 102 and 104 (FIG. 4) that define opposite manipulation segments 106 and 108 and a median section 110. For purposes of simplicity the reference numbers 106, 108 and 110 can also be used to define the corresponding underlying adhesive segments and sections of the collar 90.

As most clearly shown in FIG. 10, the collar 90 is sized with an inside diameter that is smaller than the outside diameter of the mounting wafer components 70, 76 and 84. For example, the outside diameter of the Fasson collar 90 is approximately 5¼ inches and the inside diameter approximately 3½ inches, such that the Fasson collar 90 overlays the periphery of the mounting wafer components 70, 76 and 84, but exposes a substantial portion of the release film-landing area 86 for adhesive engagement with the annular face plate 50 of the pouch 12.

Figure 5:
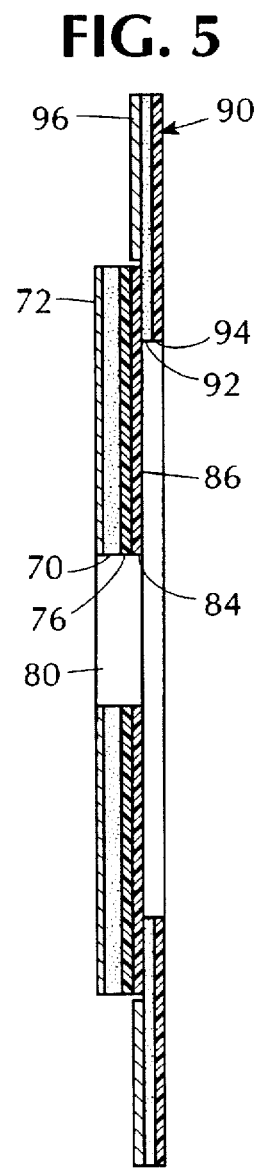
FIG. 5 is a sectional view taken on the line 5—5 of FIG. 4.

As most clearly shown in FIG. 5, the mounting wafer 14, as assembled for securement to the abdominal surface 100, includes the adhesive layer 70 covered with the removable silicone release layer 72 and backed by the foam tape 76, which is further backed by the release film layer 84. The assembled body-side mounting wafer 14 also includes the Fasson collar 90 secured to the periphery of the release film layer 84, as most clearly shown in FIG. 5. The adhesive surface 92 of the Fasson collar 82 that extends radially beyond the mounting wafer components 70, 76 and 84 is covered by the silicone release paper 96.

In using the ostomy system 10, the body-side mounting wafer 14 is first joined to the abdominal surface 100. Prior to securement of the body-side mounting wafer 14 to the abdominal surface 100, the silicone release paper 72 is removed from the abdominal adhesive layer 70 and the median section 110 of release paper 96 is removed from the Fasson collar 90. Release paper 96 remains at the opposite manipulation edge portions 106 and 108 of the Fasson collar 90. The mounting wafer 14 can then be handled by the manipulation portions 106 and 108, to locate the body-side mounting wafer opening 80, in alignment with a stoma 120.

The body-side mounting wafer 14 is secured to the abdominal surface 100 by the abdominal adhesive layer 70 and the median section 110 of the Fasson collar 90. The silicone release paper 96 still covers the manipulation portions 106 and 108 of the Fasson collar 90. Once the mounting wafer 14 is in a secured position around the stoma 120 by the abdominal adhesive layer 70 and the median section 110 of the Fasson collar 90, the remaining release paper 96 can be removed from the manipulation sections 106 and 108. The full annular adhesive layer 92 of the Fasson collar 90 that projects beyond the periphery of the mounting wafer components 70, 76 and 84 thus attaches to the abdominal surface, thereby covering any otherwise exposed edges of the abdominal adhesive layer 70.

With the body-side mounting wafer 14 satisfactorily secured to the abdominal surface 100, the pouch 12 can then be secured to the body-side mounting wafer 14. The silicone release paper 64 covering the annular face plate 50 of the pouch 12 is then removed to expose the adhesive surface 62 of the face plate. The face plate 50 can be grasped at the tab portion 54 to facilitate manipulation of the face plate 50 against the release film-landing area 86 of the body-side mounting wafer 14. The tab portion 54 helps indicate the location of the waste inlet opening 32 of the pouch 12 and thus simplifies alignment of the waste inlet opening 32 with the mounting wafer 14 and the stoma 120.

Once the pouch 12 is secured via the faceplate 50 to the mounting wafer 14, it may be desirable to adjust or reposition the pouch 12 against the mounting wafer 14. The tab portion 54 of the face plate 50 is accessible for manual grasping, as shown in FIG. 10, to peel the annular face plate 50 from the release film 84 of the body-side mounting wafer 14. The releasable qualities of the film 84 facilitate removal of the face plate 50 from the mounting wafer 14. Resecurement of the annular face plate 50 to the release film 84 of the body-side mounting wafer 14 is then accomplished in a manner similar to that previously described. The resealable qualities of the adhesive surface 62 facilitate resecurement of the face plate 50 to the mounting wafer 14.

The foam tape 60 of the annular face plate 50 and the foam tape 76 of the body-side mounting wafer 14 help ensure that the peeling of the annular face plate 50 from the body-side mounting wafer 14 is accomplished without any kinking or wrinkling of the respective engagement surfaces, including the release film 84. Thus, resecurement of the face plate 50 to the mounting wafer 14 is a smooth, surface-to-surface engagement with no residual wrinkles or kinks. Under this arrangement, a substantially leak-tight adhesive joint is provided by the adhesive coupling between the mounting wafer 14 and the annular face plate 50, even when a repositioning of the pouch 12 is performed.

Some advantages of the present invention evident from the foregoing description include a low profile repositionable ostomy pouch that is easy to manipulate. A further advantage is that the tab portion of the face plate helps manipulate securement of the face plate to the body-side mounting wafer and also serves as an approximate indicator of alignment between the face plate and the body-side mounting wafer. The use of foam layers as constituents of the body-side mounting wafer and the annular face plate provides wrinkle-resistant qualities to the face plate and the body-side mounting wafer, while maintaining a low profile characteristic for the coupling arrangement between the pouch and the mounting wafer. The ostomy system permits reliable leak-tight securement of the pouch, even when the face plate is resecured to the mounting wafer, should readjustment of the pouch relative to the mounting wafer be desirable.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An ostomy system comprising:
    a) An ostomy pouch including a pouch envelope formed of flexible plastic material defining a waste collection chamber for body waste that passes through a stoma, a waste inlet opening formed in said envelope for positioning around said stoma to permit passage of waste material from said stoma to said collection chamber, a flexible annular adhesive coupling means for said pouch on said envelope at said waste inlet opening, said pouch coupling means having a resealable coupling adhesive, a manipulation tab extending from a generally circular peripheral portion of said pouch coupling means to manipulate positioning and repositioning of said pouch coupling means around the stoma, and
    b) a generally annular body-side mounting wafer having an opening for a stoma, said mounting wafer having a biocompatible adhesive layer on one side for securement to a body surface around the stoma, said biocompatible adhesive layer having a peripheral edge and an opposite side with a release film for engagement with the resealable coupling adhesive of said pouch coupling means, such that said pouch can be secured to said mounting wafer when the resealable coupling adhesive of the pouch coupling means engages the releasable film of the mounting wafer, the adhesion between said releasable film and said resealable coupling adhesive being predetermined to permit repeated removal of said pouch coupling means from said mounting wafer, said tab facilitating manipulation, removal and resecurement of said pouch coupling means relative to said mounting wafer, and wherein said body-side mounting wafer includes support means for said releasable film for avoiding wrinkling of said releasable film when said releasable film is flexed or is separated from a coupling bond with the pouch coupling means and wherein said body-side mounting wafer further includes an annular border tape attached to a peripheral portion of said releasable film to overlap the peripheral edge of said biocompatible adhesive layer to cover said peripheral edge of said biocompatible adhesive layer.

2. The ostomy system as claimed in claim 1, wherein said releasable film has an outer circular periphery and an inner circular periphery with a landing surface defined between the outer and inner periphery for the resealable coupling adhesive of said pouch coupling means, said resealable coupling adhesive being on a substrate having an outer circular periphery and an inner circular periphery sized to fit within the outer and inner circular periphery of the releasable film to permit the resealable coupling adhesive to engage the landing surface of the releasable film.

3. The ostomy system as claimed in claim 1, wherein said releasable film extends beyond the perimeter of said resealable coupling adhesive.

4. The ostomy system as claimed in claim 1, wherein said support means is a layer of polyethylene closed cell foam of predetermined thickness.

5. The ostomy system as claimed in claim 4, wherein said polyethylene foam layer is disposed between said biocompatible adhesive layer and said releasable film of said mounting wafer.

6. The ostomy system as claimed in claim 5, wherein said biocompatible adhesive layer, said releasable film and said polyethylene foam layer are substantially co-extensive.

7. The ostomy system as claimed in claim 1, wherein said pouch coupling means is mounted on an outside surface of said pouch envelope to surround said waste inlet opening.

8. The ostomy system as claimed in claim 1, wherein said annular pouch coupling means includes support means for said resealable coupling adhesive for avoiding wrinkling of said resealable coupling adhesive when said pouch coupling means is flexed or is separated from a coupling bond with the body-side mountin wafer, said support means including a layer of polyethylene closed cell foam.

9. The ostomy system as claimed in claim 8, wherein the layer of polyethylene closed cell foam forms a substrate for said resealable coupling adhesive.

10. The ostomy system as claimed in claim 9, wherein said tab is integrally formed with said layer of polyethylene closed cell foam and said tab is an extension of said layer of polyethylene closed cell foam.

11. The ostomy system as claimed in claim 10, wherein one side of said layer of polyethylene closed cell foam is bonded to an outside surface of said pouch envelope, said tab having a first corresponding surface that corresponds to the one side of said layer of polyethylene closed cell foam, said first corresponding surface of said tab being adhesive-free, such that said tab is movable with respect to the outside surface of said pouch envelope.

12. The ostomy system as claimed in claim 11, wherein an opposite side of said layer of polyethylene closed cell foam is coated with said resealable coupling adhesive, and said tab has a second corresponding surface that corresponds to the opposite side of said layer of polyethylene closed cell foam, said second corresponding surface of said tab being rendered non-adhesive, such that said tab is freely movable and manually accessible when the resealable coupling adhesive of said pouch coupling means is engaged with the releasable film of said mounting wafer.

13. The ostomy system as claimed in claim 12, wherein the second corresponding surface of said tab is covered with a film that has a non-adhesive outside surface facing the body-side mounting wafer when the pouch coupling means is adhesively coupled to the body-side mounting wafer.

14. The ostomy system as claimed in claim 1, wherein said annular border tape has a non-adhesive surface corresponding to the release film and an adhesive surface corresponding to the biocompatible adhesive layer, a removable protective paper being provided on the adhesive surface of said annular border tape, said removable protective paper having at least two score lines that define three sections of said removable protective paper, the score lines permitting removal of each one of the sections of said removable protective paper independently of the other two sections, such that removal of one of said three sections of said removable protective paper from said body-side mounting wafer permits manipulation of said body-side mounting wafer to an attachment position on the body surface by gripping the other two sections of the annular border tape while they are covered with said protective paper.

15. The ostomy system as claimed in claim wherein said other two sections of said removable protective paper are located at opposite side edges of said annular border tape and said one section of said removable protective paper is located intermediate said other two sections to permit removal of said protective paper from said other two sections after the border tape at said one section is secured to said body surface.

16. A method for providing wrinkle-free securement, removal and resecurement of an adhesive coupling member of an ostomy pouch and a body-side mounting wafer, comprising:

a) providing the body-side mounting wafer with a landing surface formed of a releasable film, b) incorporating within the mounting wafer a first layer of polyethylene closed cell foam to support the releasable film, to avoid wrinkling of the releasable film when the releasable film is flexed or separated from a coupling bond with an ostomy pouch, c) providing an ostomy pouch with an adhesive coupling having an exposed resealable adhesive for engagement with the releasable film of the body-side mounting wafer, d) supporting the resealable adhesive with a second layer of polyethylene closed cell foam, to avoid wrinkling of the resealable adhesive when the adhesive coupling of the pouch is flexed or separated from a coupling bond with the body-side mounting wafer, e) attaching the second layer of polyethylene closed cell foam to an outside surface of the ostomy pouch, f) engaging the resealable adhesive of the pouch coupling with the releasable film of the mounting wafer, and g) forming a manipulation tab that extends from the periphery of the pouch coupling integral with the first layer of polyethylene closed cell foam for manual gripping to manipulate attachment, removal and resecurement of the pouch coupling with respect to the mounting wafer, and h) providing a film layer on the tab to inhibit stretching of said tab during gripping of the tab for manipulation of the pouch coupling.

* * * * *